(12) United States Patent
Verreck (10) Patent No.: US 10,285,948 B2
(45) Date of Patent: May 14, 2019

(54) ANTICANCER COMPOSITIONS

(71) Applicant: Aragon Pharmaceuticals, Inc., San Diego, CA (US)

(72) Inventor: Geert Verreck, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/533,229

(22) PCT Filed: Dec. 3, 2015

(86) PCT No.: PCT/US2015/063671
§ 371 (c)(1),
(2) Date: Jun. 5, 2017

(87) PCT Pub. No.: WO2016/090105
PCT Pub. Date: Jun. 9, 2016

(65) Prior Publication Data
US 2017/0360713 A1    Dec. 21, 2017

(30) Foreign Application Priority Data

Dec. 5, 2014 (EP) .................................. 14196605

(51) Int. Cl.
*A61K 9/14* (2006.01)
*A61K 9/20* (2006.01)
*A61K 31/4439* (2006.01)

(52) U.S. Cl.
CPC ............ *A61K 9/2054* (2013.01); *A61K 9/146* (2013.01); *A61K 31/4439* (2013.01)

(58) Field of Classification Search
None
See application file for complete search history.

(56) References Cited

U.S. PATENT DOCUMENTS 9,987,261 B2    6/2018  Jung et al.
2010/0310659 A1*  12/2010  Desai .................. C07D 471/04
                                                       424/486
(Continued)

FOREIGN PATENT DOCUMENTS

WO    2007126765 A2    11/2007
WO    2013152342 A1    10/2013
(Continued)

OTHER PUBLICATIONS

Beak I.H. and Kim M.S., Improved supersaturation and oral absorption of dutasteride by amorphous solid dispersions. Chem Pharm Bull (Tokyo), Nov. 30, 2012, vol. 60, No. 11, pp. 1468-1473 whole document, particularly abstract.
(Continued)

*Primary Examiner* — Aradhana Sasan (57) ABSTRACT

The present invention concerns pharmaceutical formulations of ARN-509, which can be administered to a mammal, in particular a human, suffering from an androgen receptor (AR)-related disease or condition, in particular cancer, more in particular prostate cancer, including but not limited to castration-resistant prostate cancer, metastatic castration resistant prostate cancer, chemotherapy-naive metastatic castration resistant prostate cancer, biochemically relapsed hormone sensitive prostate cancer, or high-risk, non-metastatic castration-resistant prostate cancer. In one aspect, these formulations comprise a solid dispersion of ARN-509, a poly(meth)acrylate copolymer and HPMCAS. In one aspect, the solid dispersion of ARN-509, a poly(meth) acrylate copolymer and HPMCAS is obtainable, in particular is obtained, by melt-extruding a mixture comprising ARN-509, a poly(meth)acrylate copolymer and HPMCAS and optionally subsequently milling said melt-extruded mixture. In one aspect, the solid dispersion of ARN-509, a poly(meth)acrylate copolymer and HPMCAS is obtainable, in particular is obtained, by spray drying a mixture comprising ARN-509, a poly(meth)acrylate copolymer and HPMCAS in a suitable solvent.

43 Claims, 3 Drawing Sheets

(56) References Cited

U.S. PATENT DOCUMENTS

2014/0100256 A1    4/2014  Lorenz et al.
2015/0209359 A1*   7/2015  Yaffe .................. A61K 31/4409
                                                              514/171

FOREIGN PATENT DOCUMENTS

| WO | 2013184681 A1 | 12/2013 |
| WO | 2014113260 A1 | 7/2014 |
| WO | 2015118016 A1 | 8/2015 |
| WO | WO 2015/118015 A1 * | 8/2015 ............... A61K 9/00 |

OTHER PUBLICATIONS

Jafari E., Preparation, Characterization and Dissolution of Solid Dispersion of Diclofenac Sodium Using Eudragit E-100. Journal of Applied Pharmaceutical Science, Aug. 31, 2013, vol. 3, No. 08, pp. 167-170.

Friesen D.T. et al., Hydroxypropyl Methylcellulose Acetate Succinate-Based Spray-Dried Dispersions: an overview. Mol Pharm., Dec. 1, 2008, vol. 5, No. 6, pp. 1003-1019 Whole document, particularly abstract.

Huang Y. & Dai W.G., Fundamental aspects of solid dispersion technology for poorly soluble drugs. Acta Pharm Sin B, Dec. 5, 2013, vol. 4, No. 1, pp. 18-25 Whole document, particularly abstract.

* cited by examiner

Figure 1: Powder XRD Diffraction patterns of ARN-509 Form B

Figure 2. Infrared spectrometry (microATR) of ARN-509 Form B.

Figure 3: Differential scanning calorimetry (DSC) of ARN-509 Form B.

ANTICANCER COMPOSITIONS

CROSS REFERENCE TO RELATED APPLICATIONS

This application is a national stage application of International Patent Application No. PCT/US2015/063671, filed 3 Dec. 2015, which claims priority from EP Application 14196605.1 filed 5 Dec. 2014. The complete disclosures of the aforementioned related patent applications are hereby incorporated herein by reference for all purposes.

The present invention concerns pharmaceutical formulations of ARN-509, which can be administered to a mammal, in particular a human, suffering from an androgen receptor (AR)-related disease or condition, in particular cancer, more in particular prostate cancer, including but not limited to castration-resistant prostate cancer, metastatic castration resistant prostate cancer, chemotherapy-naive metastatic castration resistant prostate cancer, biochemically relapsed hormone sensitive prostate cancer, or high-risk, non-metastatic castration-resistant prostate cancer. In one aspect, these formulations comprise a solid dispersion of ARN-509, a poly(meth)acrylate copolymer and HPMCAS. In one aspect, the solid dispersion of ARN-509, a poly(meth)acrylate copolymer and HPMCAS is obtainable, in particular is obtained, by melt-extruding a mixture comprising ARN-509, a poly(meth)acrylate copolymer and HPMCAS and optionally subsequently milling said melt-extruded mixture. In one aspect, the solid dispersion of ARN-509, a poly(meth)acrylate copolymer and HPMCAS is obtainable, in particular is obtained, by spray drying a mixture comprising ARN-509, a poly(meth)acrylate copolymer and HPMCAS in a suitable solvent.

The solid dispersion of ARN-509, a poly(meth)acrylate copolymer and HPMCAS may be further formulated with a pharmaceutically acceptable carrier into a pharmaceutical formulation, such formulation providing improved stability or improved shelf life. The formulation of the present invention provides for a fast drug release. With the formulation of the present invention the pill burden for the patient, in particular the cancer patient, can be reduced, and hence therapy adherence and therapy efficiency can be improved.

DETAILED DESCRIPTION

ARN-509 is a potent and specific antagonist of the androgen receptor (AR). ARN-509's mechanism of action is antagonism of androgen receptor signaling through inhibition of AR nuclear translocation and DNA binding to androgen response elements.

The actions of androgens with androgen receptors have been implicated in a number of diseases or conditions, such as androgen dependent cancers, virilization in women, and acne, among others. Compounds that diminish the effects of androgens with androgen receptors and/or lower the concentrations of androgen receptors find use in the treatment of diseases or conditions in which androgen receptors play a role.

AR-related diseases or conditions include, but are not limited to, benign prostate hyperplasia, hirsutism, acne, adenomas and neoplasias of the prostate, benign or malignant tumor cells containing the androgen receptor, hyperpilosity, seborrhea, endometriosis, polycystic ovary syndrome, androgenic alopecia, hypogonadism, osteoporosis, suppression of spermatogenesis, libido, cachexia, anorexia, androgen supplementation for age related decreased testosterone levels, prostate cancer, breast cancer, endometrial cancer, uterine cancer, hot flashes, Kennedy's disease muscle atrophy and weakness, skin atrophy, bone loss, anemia, arteriosclerosis, cardiovascular disease, loss of energy, loss of well-being, type 2 diabetes, and abdominal fat accumulation. Given the central role of AR in prostate cancer development and progression, ARN-509 is useful for the treatment of cancer, in particular prostate cancer, including but not limited to castration-resistant prostate cancer, metastatic castration resistant prostate cancer, chemotherapy-naive metastatic castration resistant prostate cancer, biochemically relapsed hormone sensitive prostate cancer, or high-risk, non-metastatic castration-resistant prostate cancer.

The chemical structure of ARN-509 is:

ARN-509 or 4-[7-(6-cyano-5-trifluoromethylpyridin-3-yl)-8-oxo-6-thioxo-5,7-diazaspiro[3.4]oct-5-yl]-2-fluoro-N-methylbenzamide is currently in clinical development as a nonaqueous, lipid-based solution that is filled into softgel capsules, each containing 30 mg ARN-509. The daily dose being studied is 240 mg/day by oral administration (or 8 softgel capsules). It has been found that in use, the softgel capsules containing ARN-509 have a shelf life of only 6 months and need cold chain storage.

An aspect of the invention relates to pharmaceutical formulations, in particular solid pharmaceutical formulations, more in particular solid pharmaceutical formulations for oral administration of ARN-509, where such formulations have an improved stability, a longer shelf life, provide for a fast drug release or provide for a reduced pill burden for the patient, in particular the cancer patient. The pharmaceutical formulations of the present invention provide a means to increase therapy adherence and therapy efficiency.

An aspect of the invention is a solid dispersion comprising ARN-509, a poly(meth)acrylate copolymer and HPMCAS.

Copolymers derived from esters of acrylic and methacrylic acid (poly(meth)acrylates) are known in the industry as Eudragit®. Eudragit® is the brand name for a diverse range of poly(meth)acrylate-based copolymers. Different grades are available. In an aspect of the invention, the Eudragit® in the dispersions with ARN-509 is Eudragit® L 100-55 which contains an anionic copolymer based on methacrylic acid and ethyl acrylate (CAS number 25212-88-8; Chemical/IUPAC name: Poly(methacrylic acid-co-ethyl acrylate) 1:1) (Evonik Industries). In an aspect of the invention, the Eudragit® in the dispersions with ARN-509 is Eudragit® E 100 which is a cationic copolymer based on dimethylaminoethyl methacrylate, butyl methacrylate, and methyl methacrylate (CAS number 24938-16-7; Chemical/IUPAC name: Poly(butyl methacrylate-co-(2-dimethylaminoethyl) methacrylate-co-methyl methacrylate) 1:2:1 (Evonik Industries). HPMCAS or hydroxypropyl methylcellulose acetate succinate or hypromellose acetate succinate (CAS number 71138-97-1) is a mixture of acetic acid and monosuccinic acid esters of hydroxypropylmethyl cellulose (IUPAC name: cellulose, 2-hydroxypropyl methyl ether, acetate, hydrogen butanedioate). Different grades are available differentiated based on degree/ratio of substitution (acetyl content, succinoyl content) and particle size (micronized and granular). In an aspect of the invention, the HPMCAS in the dispersions with ARN-509 is HPMCAS LG (granular grade) or HPMCAS LF (micronized grade) (Shin-Etsu Chemical Co., Ltd), in particular HPMCAS LG.

An aspect of the invention is a solid dispersion comprising ARN-509, a poly(meth)acrylate copolymer selected from Eudragit® L 100-55 and Eudragit® E 100, and HPMCAS.

An aspect of the invention is a solid dispersion comprising ARN-509, a poly(meth)acrylate copolymer selected from Eudragit® L 100-55 and Eudragit® E 100, and HPMCAS selected from HPMCAS LG and HPMCAS LF.

An aspect of the invention is a solid dispersion comprising
  a) ARN-509, Eudragit® E 100 and HPMCAS LG;
  b) ARN-509, Eudragit® E 100 and HPMCAS LF;
  c) ARN-509, Eudragit® L 100-55 and HPMCAS LG; or
  d) ARN-509, Eudragit® L 100-55 and HPMCAS LF.

An aspect of the invention is a solid dispersion consisting of ARN-509, a poly(meth)acrylate copolymer and HPMCAS.

An aspect of the invention is a solid dispersion consisting of ARN-509, a poly(meth)acrylate copolymer selected from Eudragit® L 100-55 and Eudragit® E 100, and HPMCAS.

An aspect of the invention is a solid dispersion consisting of ARN-509, a poly(meth)acrylate copolymer selected from Eudragit® L 100-55 and Eudragit® E 100, and HPMCAS selected from HPMCAS LG and HPMCAS LF.

An aspect of the invention is a solid dispersion consisting of
  a) ARN-509, Eudragit® E 100 and HPMCAS LG;
  b) ARN-509, Eudragit® E 100 and HPMCAS LF;
  c) ARN-509, Eudragit® L 100-55 and HPMCAS LG; or
  d) ARN-509, Eudragit® L 100-55 and HPMCAS LF.

A preferred grade of the poly(meth)acrylate copolymer in the solid dispersions of the invention is Eudragit® L 100-55.

A preferred grade of HPMCAS in the solid dispersions of the invention is HPMCAS LG, because of its better and safer handling properties.

In an aspect of the invention, the weight-by-weight ratio of ARN-509:(poly(meth)acrylate copolymer and HPMCAS) in the solid dispersion as described herein is in the range from 1:1 to 1:10, preferably from 1:1 to 1:5, more preferably from 1:1 to 1:3 or from 1:2 to 1:3. In an aspect of the invention, the weight-by-weight ratio of ARN-509:(poly(meth)acrylate copolymer and HPMCAS) is 1:2. In an aspect of the invention, the weight-by-weight ratio of ARN-509:(poly(meth)acrylate copolymer and HPMCAS) is 1:3. In an aspect of the invention, the weight-by-weight ratio of ARN-509:(Eudragit® L 100-55 and HPMCAS LG) is 1:2. In an aspect of the invention, the weight-by-weight ratio of ARN-509:(Eudragit® L 100-55 and HPMCAS LG) is 1:3. In an aspect of the invention, the weight-by-weight ratio of ARN-509:(Eudragit® E 100 and HPMCAS LG) is 1:2. In an aspect of the invention, the weight-by-weight ratio of ARN-509:(Eudragit® E 100 and HPMCAS LG) is 1:3. In an aspect of the invention, the weight-by-weight ratio of ARN-509:(Eudragit® L 100-55 and HPMCAS LF) is 1:2. In an aspect of the invention, the weight-by-weight ratio of ARN-509:(Eudragit® L 100-55 and HPMCAS LF) is 1:3. In an aspect of the invention, the weight-by-weight ratio of ARN-509:(Eudragit® E 100 and HPMCAS LF) is 1:2. In an aspect of the invention, the weight-by-weight ratio of ARN-509:(Eudragit® E 100 and HPMCAS LF) is 1:3.

In an aspect of the invention, the weight-by-weight ratio of poly(meth)acrylate copolymer to HPMCAS in the solid dispersion as described herein ranges from 5:95 to 95:5, in particular from 10:90 to 90:10, more in particular from 25:75 to 75:25. Preferably, the weight-by-weight ratio of poly(meth)acrylate copolymer to HPMCAS in the solid dispersion as described herein is 50:50.

An aspect of the invention is a particle consisting of a solid dispersion as described herein.

An aspect of the invention is a particle consisting of a solid dispersion comprising ARN-509, a poly(meth)acrylate copolymer and HPMCAS, in particular wherein the weight-by-weight ratio of ARN-509:(poly(meth)acrylate copolymer and HPMCAS) is 1:2 or 1:3, more in particular wherein the weight-by-weight ratio of poly(meth)acrylate copolymer to HPMCAS ranges from 25:75 to 75:25, or is 25:75, 50:50, or 75:25; 50:50 being preferred.

An aspect of the invention is a particle consisting of a solid dispersion comprising
  a) ARN-509, Eudragit® E 100 and HPMCAS LG; in particular wherein the weight-by-weight ratio of ARN-509:(Eudragit® E 100 and HPMCAS LG) is 1:2 or 1:3; more in particular wherein the weight-by-weight ratio of Eudragit® E 100:HPMCAS LG ranges from 25:75 to 75:25, or is 25:75, 50:50, or 75:25; 50:50 being preferred;
  b) ARN-509, Eudragit® E 100 and HPMCAS LF; in particular wherein the weight-by-weight ratio of ARN-509:(Eudragit® E 100 and HPMCAS LF) is 1:2 or 1:3; more in particular wherein the weight-by-weight ratio of Eudragit® E 100:HPMCAS LF ranges from 25:75 to 75:25, or is 25:75, 50:50, or 75:25; 50:50 being preferred;
  c) ARN-509, Eudragit® L 100-55 and HPMCAS LG; in particular wherein the weight-by-weight ratio of ARN-509:(Eudragit® L 100-55 and HPMCAS LG) is 1:2 or 1:3; more in particular wherein the weight-by-weight ratio of Eudragit® L 100-55:HPMCAS LG ranges from 25:75 to 75:25, or is 25:75, 50:50, or 75:25; 50:50 being preferred; or
  d) ARN-509, Eudragit® L 100-55 and HPMCAS LF; in particular wherein the weight-by-weight ratio of ARN-509:(Eudragit® L 100-55 and HPMCAS LF) is 1:2 or 1:3; more in particular wherein the weight-by-weight ratio of Eudragit® L 100-55:HPMCAS LF ranges from 25:75 to 75:25, or is 25:75, 50:50, or 75:25; 50:50 being preferred.

An aspect of the invention is a particle consisting of a solid dispersion consisting of ARN-509, a poly(meth)acrylate copolymer and HPMCAS, in particular wherein the weight-by-weight ratio of ARN-509:(poly(meth)acrylate copolymer and HPMCAS) is 1:2 or 1:3, more in particular wherein the weight-by-weight ratio of poly(meth)acrylate copolymer to HPMCAS ranges from 25:75 to 75:25, or is 25:75, 50:50, or 75:25; 50:50 being preferred.

An aspect of the invention is a particle consisting of a solid dispersion consisting of
  a) ARN-509, Eudragit® E 100 and HPMCAS LG; in particular wherein the weight-by-weight ratio of ARN-509:(Eudragit® E 100 and HPMCAS LG) is 1:2 or 1:3; more in particular wherein the weight-by-weight ratio of Eudragit® E 100:HPMCAS LG ranges from 25:75 to 75:25, or is 25:75, 50:50, or 75:25; 50:50 being preferred;
  b) ARN-509, Eudragit® E 100 and HPMCAS LF; in particular wherein the weight-by-weight ratio of ARN-509:

(Eudragit® E 100 and HPMCAS LF) is 1:2 or 1:3; more in particular wherein the weight-by-weight ratio of Eudragit® E 100:HPMCAS LF ranges from 25:75 to 75:25, or is 25:75, 50:50, or 75:25; 50:50 being preferred;

c) ARN-509, Eudragit® L 100-55 and HPMCAS LG; in particular wherein the weight-by-weight ratio of ARN-509:(Eudragit® L 100-55 and HPMCAS LG) is 1:2 or 1:3; more in particular wherein the weight-by-weight ratio of Eudragit® L 100-55:HPMCAS LG ranges from 25:75 to 75:25, or is 25:75, 50:50, or 75:25; 50:50 being preferred; or d) ARN-509, Eudragit® L 100-55 and HPMCAS LF; in particular wherein the weight-by-weight ratio of ARN-509:(Eudragit® L 100-55 and HPMCAS LF) is 1:2 or 1:3; more in particular wherein the weight-by-weight ratio of Eudragit® L 100-55:HPMCAS LF ranges from 25:75 to 75:25, or is 25:75, 50:50, or 75:25; 50:50 being preferred.

An aspect of the invention is a particle comprising a solid dispersion as described hereinabove.

An aspect of the invention is a particle comprising a solid dispersion comprising ARN-509, a poly(meth)acrylate copolymer and HPMCAS, in particular wherein the weight-by-weight ratio of ARN-509:(poly(meth)acrylate copolymer and HPMCAS) is 1:2 or 1:3, more in particular wherein the weight-by-weight ratio of poly(meth)acrylate copolymer to HPMCAS ranges from 25:75 to 75:25, or is 25:75, 50:50, or 75:25; 50:50 being preferred.

An aspect of the invention is a particle comprising a solid dispersion comprising a) ARN-509, Eudragit® E 100 and HPMCAS LG; in particular wherein the weight-by-weight ratio of ARN-509:(Eudragit® E 100 and HPMCAS LG) is 1:2 or 1:3; more in particular wherein the weight-by-weight ratio of Eudragit® E 100:HPMCAS LG ranges from 25:75 to 75:25, or is 25:75, 50:50, or 75:25; 50:50 being preferred;

b) ARN-509, Eudragit® E 100 and HPMCAS LF; in particular wherein the weight-by-weight ratio of ARN-509:(Eudragit® E 100 and HPMCAS LF) is 1:2 or 1:3; more in particular wherein the weight-by-weight ratio of Eudragit® E 100:HPMCAS LF ranges from 25:75 to 75:25, or is 25:75, 50:50, or 75:25; 50:50 being preferred;

c) ARN-509, Eudragit® L 100-55 and HPMCAS LG; in particular wherein the weight-by-weight ratio of ARN-509:(Eudragit® L 100-55 and HPMCAS LG) is 1:2 or 1:3; more in particular wherein the weight-by-weight ratio of Eudragit® L 100-55:HPMCAS LG ranges from 25:75 to 75:25, or is 25:75, 50:50, or 75:25; 50:50 being preferred; or d) ARN-509, Eudragit® L 100-55 and HPMCAS LF; in particular wherein the weight-by-weight ratio of ARN-509:(Eudragit® L 100-55 and HPMCAS LF) is 1:2 or 1:3; more in particular wherein the weight-by-weight ratio of Eudragit® L 100-55:HPMCAS LF ranges from 25:75 to 75:25, or is 25:75, 50:50, or 75:25; 50:50 being preferred.

An aspect of the invention is a particle comprising a solid dispersion consisting of ARN-509, a poly(meth)acrylate copolymer and HPMCAS, in particular wherein the weight-by-weight ratio of ARN-509:(poly(meth)acrylate copolymer and HPMCAS) is 1:2 or 1:3, more in particular wherein the weight-by-weight ratio of poly(meth)acrylate copolymer to HPMCAS ranges from 25:75 to 75:25, or is 25:75, 50:50, or 75:25; 50:50 being preferred.

An aspect of the invention is a particle comprising a solid dispersion consisting of a) ARN-509, Eudragit® E 100 and HPMCAS LG; in particular wherein the weight-by-weight ratio of ARN-509:(Eudragit® E 100 and HPMCAS LG) is 1:2 or 1:3; more in particular wherein the weight-by-weight ratio of Eudragit® E 100:HPMCAS LG ranges from 25:75 to 75:25, or is 25:75, 50:50, or 75:25; 50:50 being preferred;

b) ARN-509, Eudragit® E 100 and HPMCAS LF; in particular wherein the weight-by-weight ratio of ARN-509:(Eudragit® E 100 and HPMCAS LF) is 1:2 or 1:3; more in particular wherein the weight-by-weight ratio of Eudragit® E 100:HPMCAS LF ranges from 25:75 to 75:25, or is 25:75, 50:50, or 75:25; 50:50 being preferred;

c) ARN-509, Eudragit® L 100-55 and HPMCAS LG; in particular wherein the weight-by-weight ratio of ARN-509:(Eudragit® L 100-55 and HPMCAS LG) is 1:2 or 1:3; more in particular wherein the weight-by-weight ratio of Eudragit® L 100-55:HPMCAS LG ranges from 25:75 to 75:25, or is 25:75, 50:50, or 75:25; 50:50 being preferred; or d) ARN-509, Eudragit® L 100-55 and HPMCAS LF; in particular wherein the weight-by-weight ratio of ARN-509:(Eudragit® L 100-55 and HPMCAS LF) is 1:2 or 1:3; more in particular wherein the weight-by-weight ratio of Eudragit® L 100-55:HPMCAS LF ranges from 25:75 to 75:25, or is 25:75, 50:50, or 75:25; 50:50 being preferred.

In an aspect of the invention, the particles as described herein are obtainable, in particular are obtained, by melt-extruding a mixture comprising ARN-509, a poly(meth)acrylate copolymer and HPMCAS, and subsequently milling said melt-extruded mixture. In an aspect, the particles as described herein are obtainable, in particular are obtained, by melt-extruding a mixture consisting of ARN-509, a poly(meth)acrylate copolymer and HPMCAS, and subsequently milling said melt-extruded mixture. In an aspect, the weight-by-weight ratio of ARN-509:(poly(meth)acrylate copolymer and HPMCAS) is 1:2 or 1:3. In an aspect, the weight-by-weight ratio of poly(meth)acrylate copolymer:HPMCAS ranges from 25:75 to 75:25, or is 25:75, 50:50, or 75:25; 50:50 being preferred.

In an aspect of the invention, the particles as described herein are obtainable, in particular are obtained, by melt-extruding a mixture comprising ARN-509, Eudragit® L 100-55 and HPMCAS LG, and subsequently milling said melt-extruded mixture. In an aspect, the particles as described herein are obtainable, in particular are obtained, by melt-extruding a mixture consisting of ARN-509, Eudragit® L 100-55 and HPMCAS LG, and subsequently milling said melt-extruded mixture. In an aspect, the weight-by-weight ratio of ARN-509:(Eudragit® L 100-55 and HPMCAS LG) is 1:2 or 1:3. In an aspect, the weight-by-weight ratio of Eudragit® L 100-55:HPMCAS LG ranges from 25:75 to 75:25, or is 25:75, 50:50, or 75:25; 50:50 being preferred.

In an aspect of the invention, the particles as described herein are obtainable, in particular are obtained, by melt-extruding a mixture comprising ARN-509, Eudragit® E 100 and HPMCAS LG, and subsequently milling said melt-extruded mixture. In an aspect, the particles as described herein are obtainable, in particular are obtained, by melt-extruding a mixture consisting of ARN-509, Eudragit® E 100 and HPMCAS LG, and subsequently milling said melt-extruded mixture. In an aspect, the weight-by-weight ratio of ARN-509:(Eudragit® E 100 and HPMCAS LG) is 1:2 or 1:3. In an aspect, the weight-by-weight ratio of Eudragit® E 100:HPMCAS LG ranges from 25:75 to 75:25, or is 25:75, 50:50, or 75:25; 50:50 being preferred.

In an aspect of the invention, the particles as described herein are obtainable, in particular are obtained, by melt-extruding a mixture comprising ARN-509, Eudragit® L 100-55 and HPMCAS LF, and subsequently milling said melt-extruded mixture. In an aspect, the particles as described herein are obtainable, in particular are obtained, by melt-extruding a mixture consisting of ARN-509, Eudragit® L 100-55 and HPMCAS LF, and subsequently milling said melt-extruded mixture. In an aspect, the weight-by-weight ratio of ARN-509:(Eudragit® L 100-55 and HPMCAS LF) is 1:2 or 1:3. In an aspect, the weight-by-weight ratio of Eudragit® L 100-55:HPMCAS LF ranges from 25:75 to 75:25, or is 25:75, 50:50, or 75:25; 50:50 being preferred.

In an aspect of the invention, the particles as described herein are obtainable, in particular are obtained, by melt-extruding a mixture comprising ARN-509, Eudragit® E 100 and HPMCAS LF, and subsequently milling said melt-extruded mixture. In an aspect, the particles as described herein are obtainable, in particular are obtained, by melt-extruding a mixture consisting of ARN-509, Eudragit® E 100 and HPMCAS LF, and subsequently milling said melt-extruded mixture. In an aspect, the weight-by-weight ratio of ARN-509:(Eudragit® E 100 and HPMCAS LF) is 1:2 or 1:3. In an aspect, the weight-by-weight ratio of Eudragit® E 100:HPMCAS LF ranges from 25:75 to 75:25, or is 25:75, 50:50, or 75:25; 50:50 being preferred.

In an aspect of the invention, the particles as described herein are obtainable, in particular are obtained, by spray drying a mixture comprising ARN-509, a poly(meth)acrylate copolymer and HPMCAS in a suitable solvent. In an aspect, the particles as described herein are obtainable, in particular are obtained, by spray drying a mixture consisting of ARN-509, a poly(meth)acrylate copolymer and HPMCAS in a suitable solvent. In an aspect, the weight-by-weight ratio of ARN-509:(poly(meth)acrylate copolymer and HPMCAS) is 1:2 or 1:3. In an aspect, the weight-by-weight ratio of poly(meth)acrylate copolymer:HPMCAS ranges from 25:75 to 75:25, or is 25:75, 50:50, or 75:25; 50:50 being preferred.

In an aspect of the invention, the particles as described herein are obtainable, in particular are obtained, by spray drying a mixture comprising ARN-509, Eudragit® L 100-55 and HPMCAS LG in a suitable solvent. In an aspect, the particles as described herein are obtainable, in particular are obtained, by spray drying a mixture consisting of ARN-509, Eudragit® L 100-55 and HPMCAS LG in a suitable solvent. In an aspect, the weight-by-weight ratio of ARN-509:(Eudragit® L 100-55 and HPMCAS LG) is 1:2 or 1:3. In an aspect, the weight-by-weight ratio of Eudragit® L 100-55:HPMCAS LG ranges from 25:75 to 75:25, or is 25:75, 50:50, or 75:25; 50:50 being preferred.

In an aspect of the invention, the particles as described herein are obtainable, in particular are obtained, by spray drying a mixture comprising ARN-509, Eudragit® E 100 and HPMCAS LG in a suitable solvent. In an aspect, the particles as described herein are obtainable, in particular are obtained, by spray drying a mixture consisting of ARN-509, Eudragit® E 100 and HPMCAS LG in a suitable solvent. In an aspect, the weight-by-weight ratio of ARN-509:(Eudragit® E 100 and HPMCAS LG) is 1:2 or 1:3. In an aspect, the weight-by-weight ratio of Eudragit® E 100:HPMCAS LG ranges from 25:75 to 75:25, or is 25:75, 50:50, or 75:25; 50:50 being preferred.

In an aspect of the invention, the particles as described herein are obtainable, in particular are obtained, by spray drying a mixture comprising ARN-509, Eudragit® L 100-55 and HPMCAS LF in a suitable solvent. In an aspect, the particles as described herein are obtainable, in particular are obtained, by spray drying a mixture consisting of ARN-509, Eudragit® L 100-55 and HPMCAS LF in a suitable solvent. In an aspect, the weight-by-weight ratio of ARN-509:(Eudragit® L 100-55 and HPMCAS LF) is 1:2 or 1:3. In an aspect, the weight-by-weight ratio of Eudragit® L 100-55:HPMCAS LF ranges from 25:75 to 75:25, or is 25:75, 50:50, or 75:25; 50:50 being preferred.

In an aspect of the invention, the particles as described herein are obtainable, in particular are obtained, by spray drying a mixture comprising ARN-509, Eudragit® E 100 and HPMCAS LF in a suitable solvent. In an aspect, the particles as described herein are obtainable, in particular are obtained, by spray drying a mixture consisting of ARN-509, Eudragit® E 100 and HPMCAS LF in a suitable solvent. In an aspect, the weight-by-weight ratio of ARN-509:(Eudragit® E 100 and HPMCAS LF) is 1:2 or 1:3. In an aspect, the weight-by-weight ratio of Eudragit® E 100:HPMCAS LF ranges from 25:75 to 75:25, or is 25:75, 50:50, or 75:25; 50:50 being preferred.

An aspect of the invention is a pharmaceutical formulation comprising a pharmaceutically acceptable carrier and a solid dispersion as described herein.

An aspect of the invention is a pharmaceutical formulation comprising a pharmaceutically acceptable carrier and a particle, in particular particles, as described herein.

An aspect of the invention is a pharmaceutical formulation comprising a pharmaceutically acceptable carrier and a solid dispersion, said solid dispersion comprising ARN-509, a poly(meth)acrylate copolymer and HPMCAS. An aspect of the invention is a pharmaceutical formulation comprising a pharmaceutically acceptable carrier and a solid dispersion, said solid dispersion consisting of ARN-509, a poly(meth)acrylate copolymer and HPMCAS. In an aspect, the weight-by-weight ratio of ARN-509:(poly(meth)acrylate copolymer and HPMCAS) is 1:2 or 1:3. In an aspect, the weight-by-weight ratio of poly(meth)acrylate copolymer:HPMCAS ranges from 25:75 to 75:25, or is 25:75, 50:50, or 75:25; 50:50 being preferred.

An aspect of the invention is a pharmaceutical formulation comprising a pharmaceutically acceptable carrier and a solid dispersion, said solid dispersion comprising ARN-509, Eudragit® L 100-55 and HPMCAS LG. An aspect of the invention is a pharmaceutical formulation comprising a pharmaceutically acceptable carrier and a solid dispersion, said solid dispersion consisting of ARN-509, Eudragit® L 100-55 and HPMCAS LG. In an aspect, the weight-by-weight ratio of ARN-509:(Eudragit® L 100-55 and HPMCAS LG) is 1:2 or 1:3. In an aspect, the weight-by-weight ratio of Eudragit® L 100-55:HPMCAS LG ranges from 25:75 to 75:25, or is 25:75, 50:50, or 75:25; 50:50 being preferred.

An aspect of the invention is a pharmaceutical formulation comprising a pharmaceutically acceptable carrier and a solid dispersion, said solid dispersion comprising ARN-509, Eudragit® E 100 and HPMCAS LG. An aspect of the invention is a pharmaceutical formulation comprising a pharmaceutically acceptable carrier and a solid dispersion, said solid dispersion consisting of ARN-509, Eudragit® E 100 and HPMCAS LG. In an aspect, the weight-by-weight ratio of ARN-509:(Eudragit® E 100 and HPMCAS LG) is 1:2 or 1:3. In an aspect, the weight-by-weight ratio of Eudragit® E 100:HPMCAS LG ranges from 25:75 to 75:25, or is 25:75, 50:50, or 75:25; 50:50 being preferred.

An aspect of the invention is a pharmaceutical formulation comprising a pharmaceutically acceptable carrier and a solid dispersion, said solid dispersion comprising ARN-509, Eudragit® L 100-55 and HPMCAS LF. An aspect of the invention is a pharmaceutical formulation comprising a pharmaceutically acceptable carrier and a solid dispersion, said solid dispersion consisting of ARN-509, Eudragit® L 100-55 and HPMCAS LF. In an aspect, the weight-byweight ratio of ARN-509:(Eudragit® L 100-55 and HPM-CAS LF) is 1:2 or 1:3. In an aspect, the weight-by-weight ratio of Eudragit® L 100-55:HPMCAS LF ranges from 25:75 to 75:25, or is 25:75, 50:50, or 75:25; 50:50 being preferred.

An aspect of the invention is a pharmaceutical formulation comprising a pharmaceutically acceptable carrier and a solid dispersion, said solid dispersion comprising ARN-509, Eudragit® E 100 and HPMCAS LF. An aspect of the invention is a pharmaceutical formulation comprising a pharmaceutically acceptable carrier and a solid dispersion, said solid dispersion consisting of ARN-509, Eudragit® E 100 and HPMCAS LF. In an aspect, the weight-by-weight ratio of ARN-509:(Eudragit® E 100 and HPMCAS LF) is 1:2 or 1:3. In an aspect, the weight-by-weight ratio of Eudragit® E 100:HPMCAS LF ranges from 25:75 to 75:25, or is 25:75, 50:50, or 75:25; 50:50 being preferred.

An aspect of the invention is a pharmaceutical formulation comprising a pharmaceutically acceptable carrier and a particle, in particular particles, comprising a solid dispersion, said solid dispersion comprising ARN-509, a poly(meth)acrylate copolymer and HPMCAS. An aspect of the invention is a pharmaceutical formulation comprising a pharmaceutically acceptable carrier and a particle, in particular particles, comprising a solid dispersion, said solid dispersion consisting of ARN-509, a poly(meth)acrylate copolymer and HPMCAS. In an aspect, the weight-by-weight ratio of ARN-509:(poly(meth)acrylate copolymer and HPMCAS) is 1:2 or 1:3. In an aspect, the weight-by-weight ratio of poly(meth)acrylate copolymer:HPMCAS ranges from 25:75 to 75:25, or is 25:75, 50:50, or 75:25; 50:50 being preferred. In an aspect, the particle is obtainable, in particular is obtained, by spray drying as described herein. In an aspect, the particle is obtainable, in particular is obtained, by melt extrusion as described herein. In an aspect, the poly(meth)acrylate copolymer is selected from Eudragit® L 100-55 and Eudragit® E 100. In an aspect the HPMCAS is selected from HPMCAS LG and HPMCAS LF.

An aspect of the invention is a pharmaceutical formulation comprising a pharmaceutically acceptable carrier and a particle, in particular particles, consisting of a solid dispersion, said solid dispersion comprising ARN-509, a poly(meth)acrylate copolymer and HPMCAS. An aspect of the invention is a pharmaceutical formulation comprising a pharmaceutically acceptable carrier and a particle, in particular particles, consisting of a solid dispersion, said solid dispersion consisting of ARN-509, a poly(meth)acrylate copolymer and HPMCAS. In an aspect, the weight-by-weight ratio of ARN-509:(poly(meth)acrylate copolymer and HPMCAS) is 1:2 or 1:3. In an aspect, the weight-by-weight ratio of poly(meth)acrylate copolymer:HPMCAS ranges from 25:75 to 75:25, or is 25:75, 50:50, or 75:25; 50:50 being preferred. In an aspect, the particle is obtainable, in particular is obtained, by spray drying as described herein. In an aspect, the particle is obtainable, in particular is obtained, by melt extrusion as described herein. In an aspect, the poly(meth)acrylate copolymer is selected from Eudragit® L 100-55 and Eudragit® E 100. In an aspect the HPMCAS is selected from HPMCAS LG and HPMCAS LF.

An aspect of the invention is a solid dispersion as described herein wherein no surfactant is present.

An aspect of the invention is a particle as described herein wherein no surfactant is present.

An aspect of the invention is a pharmaceutical formulation as described herein wherein no surfactant is present.

An aspect of the invention is a solid dispersion as described herein wherein ARN-509 is the only active pharmaceutical ingredient.

An aspect of the invention is a particle as described herein wherein ARN-509 is the only active pharmaceutical ingredient.

An aspect of the invention is a pharmaceutical formulation as described herein wherein ARN-509 is the only active pharmaceutical ingredient.

In the solid dispersions or particles or pharmaceutical formulations as described herein ARN-509 is present in base form or as a pharmaceutically acceptable addition salt, in particular as a pharmaceutically acceptable acid addition salt. Preferably, ARN-509 is present in base form.

The pharmaceutically acceptable addition salts are meant to comprise the therapeutically active non-toxic salt forms. The acid addition salt forms can be obtained by treating the base form of ARN-509 with an appropriate acid, such as inorganic acids, including but not limited to, hydrohalic acids, e.g. hydrochloric acid, hydrobromic acid and the like acids; sulfuric acid; nitric acid; phosphoric acid; metaphosphoric acid and the like acids; or organic acids, including but not limited to, acetic acid, trifluoroacetic acid, trimethylacetic acid, propanoic acid, hydroxyacetic acid, 2-hydroxypropanoic acid, 2-oxopropanoic acid, glycolic acid, oxalic acid, malonic acid, succinic acid, maleic acid, fumaric acid, malic acid, mandelic acid, tartaric acid, 2-hydroxy-1,2,3-propanetricarboxylic acid, methanesulfonic acid, ethanesulfonic acid, 1,2-ethanedisulfonic acid, 2-hydroxyethanesulfonic acid, benzoic acid, cinnamic acid, hydrocinnamic acid, benzenesulfonic acid, 4-methylbenzene-sulfonic acid, 2-naphthalenesulfonic acid, cyclohexanesulfamic acid, 2-hydroxybenzoic acid, 4-amino-2-hydroxybenzoic acid, hexanoic acid, cyclopentanepropionic acid, 3-(4-hydroxybenzoyl)benzoic acid, 4-methylbicyclo-[2.2.2]oct-2-ene-1-carboxylic acid, glucoheptonic acid, tertiary butylacetic acid, lauryl sulfuric acid, gluconic acid, glutamic acid, hydroxynaphthoic acid, stearic acid, muconic acid, butyric acid, phenylacetic acid, phenylbutyric acid, valproic acid, and the like acids.

Conversely said salt forms can be converted by treatment with an appropriate base into the free base form.

Also included are the hydrates, the solvent addition forms and mixtures thereof which ARN-509 and its salts are able to form. Examples of such forms are e.g. hydrates, alcoholates and the like, for instance an ethanolate.

In general, doses employed for adult human treatment are typically in the range from 0.01 mg to 5000 mg per day. In one aspect, doses employed for adult human treatment are from about 1 mg to about 1000 mg per day. In another aspect, doses employed for adult human treatment are from about 100 mg to about 500 mg per day. In another aspect, the dose employed for adult human treatment is 240 mg per day. The exact dosage and frequency of administration of ARN-509 may depend on the particular condition being treated, the severity of the condition being treated, the age, weight and general physical condition of the particular patient as well as other medication the individual may be taking, as is known to those skilled in the art. Furthermore, it is evident that said daily amounts may be lowered or increased depending on the response of the treated subject and/or depending on the evaluation of the physician prescribing ARN-509. The doses mentioned herein are therefore only a guideline and are not intended to limit the scope or use of the invention to any extent. In an aspect of the invention, the daily dose is conveniently presented in a single dose or in divided doses administered simultaneously (or over a short period of time) or at appropriate intervals, for example as two, three, four or more sub-doses per day. In an aspect of the invention, the daily dose is administered in 4 divided doses. In an aspect of the invention, the daily dose is administered in 4 divided doses administered simultaneously (or over a short period of time). In an aspect of the invention, the daily dose is administered in 3 divided doses. In an aspect of the invention, the daily dose is administered in 3 divided doses administered simultaneously (or over a short period of time). In an aspect of the invention, the daily dose is administered in 2 divided doses. In an aspect of the invention, the daily dose is administered in 2 divided doses administered simultaneously (or over a short period of time).

In an aspect of the invention, the pharmaceutical formulation comprises 240 mg of ARN-509.

In an aspect of the invention, the pharmaceutical formulation comprises 120 mg of ARN-509.

In an aspect of the invention, the pharmaceutical formulation comprises 60 mg of ARN-509.

In an aspect of the invention, the pharmaceutical formulation comprises 240 mg of ARN-509. The pharmaceutical formulation is administered once daily.

In an aspect of the invention, the pharmaceutical formulation comprises 120 mg of ARN-509. Two of said formulations are administered daily, preferably simultaneously (or over a short period of time).

In an aspect of the invention, the pharmaceutical formulation comprises 60 mg of ARN-509. Four of said formulations are administered daily, preferably simultaneously (or over a short period of time).

The formulation of the present invention can also be used in combination with another anticancer agent, in particular with another anti prostate cancer agent, more in particular with an androgen biosynthesis inhibitor, that inhibits 17 α-hydroxylase/C17,20-lyase (CYP17), in particular abiraterone acetate. The formulation of the present invention can further be combined with prednisone.

Thus, the present invention also relates to a combination of a pharmaceutical formulation according to the invention and another anticancer agent, in particular another anti prostate cancer agent, more in particular an androgen biosynthesis inhibitor, that inhibits 17 α-hydroxylase/C17,20-lyase (CYP17), in particular abiraterone acetate.

Said combination may further comprise prednisone.

The term "a solid dispersion" means a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermo-dynamics, such a solid dispersion will be called "a solid solution" herein. Solid solutions are preferred physical systems because the components therein are usually readily bioavailable to the organisms to which they are administered. This advantage can probably be explained by the ease with which said solid solutions can form liquid solutions when contacted with a liquid medium such as gastric juice. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to a system in a solid state comprising at least two components (a) (active ingredient) and (b) (polymer (poly(meth)acrylate copolymer and HPMCAS)) and having domains or small regions wherein amorphous, microcrystalline or crystalline (a), or amorphous, microcrystalline or crystalline (b), or both, are dispersed more or less evenly in another phase comprising (b), or (a), or a solid solution comprising (a) and (b). Said domains are regions distinctively marked by some physical feature, small in size compared to the size of the system as a whole, and evenly and randomly distributed throughout the system.

Preferred are solid dispersions or particles as described herein wherein ARN-509 is in a non-crystalline phase as these have an intrinsically faster dissolution rate than those wherein part or all of ARN-509 is in a microcrystalline or crystalline form.

Alternatively, the solid dispersions may be in the form of a dispersion wherein amorphous or microcrystalline ARN-509 or amorphous or microcrystalline poly(meth)acrylate copolymer or amorphous or microcrystalline HPMCAS is dispersed more or less evenly in a solid solution comprising ARN-509, a poly(meth)acrylate copolymer and HPMCAS.

In an aspect of the invention ARN-509 is present in the solid dispersions as described herein in amorphous form.

In an aspect of the invention the solid dispersion as described herein is a solid solution.

Various techniques exist for preparing the solid dispersions of the invention including melt-extrusion (e.g. hot melt extrusion), spray-drying and solution-evaporation, in particular hot melt-extrusion and spray-drying, spray-drying being preferred.

The particles according to the invention can be prepared by first preparing a solid dispersion of the components, and then optionally grinding or milling said dispersion.

The melt-extrusion process comprises the following steps:

a) mixing ARN-509, a poly(meth)acrylate copolymer and HPMCAS, b) optionally blending additives with the thus obtained mixture, c) heating the thus obtained blend until one obtains a homogenous melt, d) forcing the thus obtained melt through one or more nozzles; and e) cooling the melt till it solidifies.

The terms "melt" and "melting" do not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

One important parameter of melt extrusion is the temperature at which the melt-extruder is operating. For the melt extrusion process of the present invention, the operating temperature preferably ranges between about 160° C. and about 190° C., more preferably ranges between about 160° C. and 175° C. The lower temperature limit is defined by the point at which ARN-509 is still melting during extrusion with a given set of extrusion conditions. When ARN-509 is not completely molten, the extrudate may not provide the desired bioavailability. When the viscosity of the mixture is too high, the process of melt extrusion will be difficult. At higher temperatures the components may decompose to an unacceptable level. A person skilled in the art will recognize the most appropriate temperature range to be used.

The throughput rate is also of importance because the components may start to decompose when they remain too long in contact with the heating element.

It will be appreciated that the person skilled in the art will be able to optimize the parameters of the melt extrusion process within the above given ranges. The working temperatures will also be determined by the kind of extruder or the kind of configuration within the extruder that is used. Most of the energy needed to melt, mix and dissolve the components in the extruder can be provided by the heating elements. However, the friction of the material within the extruder may also provide a substantial amount of energy to the mixture and aid in the formation of a homogenous melt of the components.

A person skilled in the art will recognize the most appropriate extruder, such as, for example, a single screw, a twin screw extruder or a multi-screw extruder, for the preparation of the subject-matter of the present invention.

Spray-drying of a mixture of the components in a suitable solvent also yields a solid dispersion of said components or particles comprising or consisting of a solid dispersion of said components and may be a useful alternative to the melt-extrusion process, particularly in those cases where the poly(meth)acrylate copolymer or the HPMCAS are not sufficiently stable to withstand the extrusion conditions and where residual solvent can effectively be removed from the solid dispersion. Yet another possible preparation consists of preparing a mixture of the components in a suitable solvent, pouring said mixture onto a large surface so as to form a thin film, and evaporating the solvent therefrom.

Solvents suitable for spray-drying can be any organic solvent in which ARN-509, a poly(meth)acrylate copolymer, in particular Eudragit® L 100-55 or Eudragit® E 100, and HPMCAS, in particular HPMCAS LG or HPMCAS LF, are miscable. In an aspect of the invention, the boiling point of the solvent is lower than the Tg (glass transition temperature) of the solid dispersion. In addition, the solvent should have relatively low toxicity and be removed from the dispersion to a level that is acceptable according to The International Committee on Harmonization (ICH) guidelines. Removal of solvent to this level may require a post drying step such as for instance tray-drying, subsequent to the spray-drying process. Solvents include alcohols such as methanol, ethanol, n-propanol, iso-propanol, and butanol, in particular methanol; ketones such as acetone, methyl ethyl ketone and methyl iso-butyl ketone; esters such as ethyl acetate and propylacetate; and various other solvents such as acetonitrile, dichloromethane, toluene, and 1,1,1-trichloroethane. Lower volatility solvents such as dimethyl acetamide or dimethylsulfoxide can also be used. In an aspect of the invention, the solvent suitable for spray drying is a mixture of solvents. In an aspect of the invention the solvent for spray drying is a mixture of an alcohol and acetone, in particular a mixture of methanol and acetone, more in particular a mixture of methanol and acetone 1:9 (w:w). In an aspect of the invention the solvent for spray drying is a mixture of an alcohol and dichloromethane, in particular a mixture of methanol and dichloromethane, more in particular a mixture of methanol and dichloromethane 6:4 (w:w) or 5:5 (w:w), 5:5 (w:w) being preferred.

The particles as described herein have a $d^{50}$ of about 1500 µm, of about 1000 µm, of about 500 µm, of about 400 µm, of about 250 µm, of about 200 µm, of about 150 µm, of about 125 µm, of about 100 µm, of about 70 µm, of about 65 µm, of about 60 µm, of about 55 µm, of about 50 µm, of about 45 µm, of about 40 µm, of about 35 µm, of about 30 µm, of about 25 µm, or of about 20 µm. Particles obtained by spray drying have preferably a $d^{50}$-value falling in the range from about 20 µm to about 100 µm, in particular a $d^{50}$-value falling in the range from about 20 µm to about 70 µm, more in particular a $d^{50}$-value of about 20 µm, of about 25 µm, of about 30 µm, of about 35 µm, of about 40 µm, of about 45 µm, of about 50 µm, of about 55 µm, of about 60 µm, of about 65 µm, or of about 70 µm.

As used herein, the term $d^{50}$ has its conventional meaning as known to the person skilled in the art and can be measured by art-known particle size measuring techniques such as, for example, sedimentation field flow fractionation, photon correlation spectroscopy, laser diffraction or disk centrifugation. The $d^{50}$ mentioned herein may be related to volume distributions of the particles. In that instance, by "a $d^{50}$ of 50 µm" it is meant that at least 50% of the volume of the particles has a particle size of less than 50 µm. The same applies to the other particle sizes mentioned. In a similar manner, the $d^{50}$ particle size may be related to weight distributions of the particles. In that instance, by "$d^{50}$ of 50 µm" it is meant that at least 50% of the weight of the particles has a particle size of less than 50 µm. The same applies to the other particle sizes mentioned. Usually volume and weight distribution result in the same or about the same value for the average particle size.

The particle size can be an important factor determining the tabletting speed, in particular the flowability and therefore the manufacturability on a large scale of a particular dosage form or formulation, and the quality of the final product. For instance, for capsules, the particle size may range preferably from about 100 to about 1500 µm ($d^{50}$); for tablets the particle size is preferably less than 250 µm, more preferably less than 100 µm ($d^{50}$). Too small particles (<10-20 µm) often cause sticking on the tablet punches and manufacturability issues.

The particles or solid dispersions as described herein may further comprise one or more pharmaceutically acceptable excipients such as, for example, plasticizers, flavors, colorants, preservatives and the like. Especially in case of preparation by hot melt extrusion, said excipients should not be heat-sensitive, in other words, they should not show any appreciable degradation or decomposition at the working temperature of the melt-extruder.

Suitable plasticizers are pharmaceutically acceptable and include low molecular weight polyalcohols such as ethylene glycol, propylene glycol, 1,2 butylene glycol, 2,3-butylene glycol, styrene glycol; polyethylene glycols such as diethylene glycol, triethylene glycol, tetraethylene glycol; other polyethylene glycols having a molecular weight lower than 1,000 g/mol; polypropylene glycols having a molecular weight lower than 200 g/mol; glycol ethers such as monopropylene glycol monoisopropyl ether; propylene glycol monoethyl ether; diethylene glycol monoethyl ether; ester type plasticizers such as triethyl citrate, sorbitol lactate, ethyl lactate, butyl lactate, ethyl glycolate, allyl glycollate; and amines such as monoethanolamine, diethanolamine, triethanolamine, monoisopropanolamine; triethylenetetramine, 2-amino-2-methyl-1,3-propanediol and the like. Of these, the low molecular weight polyethylene glycols, ethylene glycol, low molecular weight polypropylene glycols and especially propylene glycol are preferred.

In an aspect of the invention, the particles or solid dispersions as described herein do not contain a plasticizer.

The solid dispersions or the particles of the present invention can be formulated into pharmaceutical formulations comprising a therapeutically effective amount of ARN- 509. Although, at first instance, pharmaceutical formulations for oral administration such as tablets and capsules are envisaged, the solid dispersions or the particles of the present invention can also be used to prepare pharmaceutical formulations e.g. for rectal administration. Preferred formulations are those adapted for oral administration shaped as a tablet. They can be produced by conventional tabletting techniques with conventional ingredients or excipients (pharmaceutically acceptable carrier) and with conventional tabletting machines. In order to facilitate the swallowing of such a formulation by a mammal, it is advantageous to give the formulations, in particular tablets, an appropriate shape. A film coat on the tablet may further contribute to the ease with which it can be swallowed.

The formulations of the invention, in particular the tablets, may include one or more conventional excipients (pharmaceutically acceptable carrier) such as disintegrants, diluents, fillers, binders, buffering agents, lubricants, glidants, thickening agents, sweetening agents, flavors, and colors. Some excipients can serve multiple purposes. Preferably, the formulations of the present invention include a disintegrant, a diluent or filler, a lubricant and glidant.

Suitable disintegrants are those that have a large coefficient of expansion. Examples thereof are hydrophilic, insoluble or poorly water-soluble crosslinked polymers such as crospovidone (crosslinked polyvinylpyrrolidone) and croscarmellose sodium (crosslinked sodium carboxymethylcellulose). The amount of disintegrant in the tablets according to the present invention may conveniently range from about 3 to about 15% (w/w) and preferably range from about 3 to 7%, in particular is about 5% (w/w). Because disintegrants by their nature yield sustained release formulations when employed in bulk, it is advantageous to dilute them with an inert substance called a diluent or filler.

A variety of materials may be used as diluents or fillers. Examples are lactose monohydrate, anhydrous lactose, sucrose, dextrose, mannitol, sorbitol, starch, cellulose (e.g. micro-crystalline cellulose (Avicel™), silicified microcrystalline cellulose), dihydrated or anhydrous dibasic calcium phosphate, and others known in the art, and mixtures thereof (e.g. spray-dried mixture of lactose monohydrate (75%) with microcrystalline cellulose (25%) which is commercially available as Microcelac™). Preferred is microcrystalline cellulose and silicified microcrystalline cellulose. The amount of diluent or filler in the tablets may conveniently range from about 20% to about 70% (w/w) and preferably ranges from about 55% to about 60% (w/w).

Lubricants and glidants can be employed in the manufacture of certain dosage forms, and will usually be employed when producing tablets. Examples of lubricants and glidants are hydrogenated vegetable oils, e.g hydrogenated Cottonseed oil, magnesium stearate, stearic acid, sodium lauryl sulfate, magnesium lauryl sulfate, colloidal silica, colloidal anhydrous silica talc, mixtures thereof, and others known in the art. Interesting lubricants are magnesium stearate, and mixtures of magnesium stearate with colloidal silica. A preferred lubricant is magnesium stearate. A preferred glidant is colloidal anhydrous silica.

Glidants generally comprise 0.2 to 7.0% of the total tablet weight, in particular 0.5 to 1.5%, more in particular 1 to 1.5% (w/w).

Lubricants generally comprise 0.2 to 7.0% of the total tablet weight, in particular 0.2 to 1%, more in particular 0.5 to 1% (w/w).

Other excipients such as coloring agents and pigments may also be added to the formulations of the invention. Coloring agents and pigments include titanium dioxide and dyes suitable for food. A coloring agent is an optional ingredient in the formulation of the invention, but when used the coloring agent can be present in an amount up to 3.5% based on the total tablet weight.

Flavors are optional in the formulation and may be chosen from synthetic flavor oils and flavoring aromatics or natural oils, extracts from plants leaves, flowers, fruits and so forth and combinations thereof. These may include cinnamon oil, oil of wintergreen, peppermint oils, bay oil, anise oil, *eucalyptus*, thyme oil. Also useful as flavors are vanilla, citrus oil, including lemon, orange, grape, lime and grapefruit, and fruit essences, including apple, banana, pear, peach, strawberry, raspberry, cherry, plum, pineapple, apricot and so forth, The amount of flavor may depend on a number of factors including the organoleptic effect desired. Generally the flavor will be present in an amount from about 0% to about 3% (w/w).

As known in the art, tablet blends may be dry-granulated or wet-granulated before tabletting. The tabletting process itself is otherwise standard and readily practised by forming a tablet from desired blend or mixture of ingredients into the appropriate shape using a conventional tablet press.

Tablets of the present invention may further be film-coated e.g. to improve taste, to provide ease of swallowing and an elegant appearance. Many suitable polymeric film-coating materials are known in the art. A preferred film-coating material is Opadry II 85F210036 Green. Other suitable film-forming polymers also may be used herein, including, hydroxypropylcellulose, hydroxypropyl methylcellulose (HPMC), especially HPMC 2910 5 mPa·s, and acrylate-methacrylate copolymers. Besides a film-forming polymer, the film coat may further comprise a plasticizer (e.g. propylene glycol) and optionally a pigment (e.g. titanium dioxide). The film-coating suspension also may contain talc as an anti-adhesive. In tablets according to the invention, the film coat in terms of weight preferably accounts for about 3% (w/w) or less of the total tablet weight.

Preferred formulations are those wherein the weight of the particles or solid dispersions as described herein ranges from 20 to 40%, in particular from 30 to 40% of the total weight of the formulation.

The present invention further concerns a process of preparing solid dispersions as described herein, comprising blending ARN-509, a poly(meth)acrylate copolymer and HPMCAS, and extruding said blend at a temperature in the range from about 160° C. to about 190° C.

The present invention further concerns a process of preparing particles as described herein, comprising blending ARN-509, a poly(meth)acrylate copolymer and HPMCAS, extruding said blend at a temperature in the range from about 160° C. to about 190° C., grinding the extrudate, and optionally sieving the particles.

Suitable extruders that may be used are the Haake mini-extruder, Leistritz 18 mm extruder, and the Leistritz 27 mm extruder.

The present invention further concerns a process of preparing particles or solid dispersions as described herein comprising mixing ARN-509, a poly(meth)acrylate copolymer and HPMCAS, in a suitable solvent and spray drying said mixture. In an aspect, the suitable solvent is a mixture of dichloromethane and methanol. In an aspect, the suitable solvent is a mixture of dichloromethane and methanol wherein the ratio of dichloromethane to methanol in the mixture is 4:6 (w/w) or 5:5 (w/w), 5:5 (w/w) being preferred.

A preferred crystalline form of ARN-509 for preparing the solid dispersions or particles as described herein is Form B, which is an anhydrous crystalline form (see hereinafter and reference is also made to WO2013/184681, which is incorporated herein by reference).

It is another object of the invention to provide a process of preparing a pharmaceutical formulation as described herein, in particular in the form of a tablet or a capsule, characterized by blending a therapeutically effective amount of a solid dispersion or particles as described herein, with a pharmaceutically acceptable carrier and compressing said blend into tablets or filling said blend in capsules.

Further, this invention concerns a solid dispersion or particles as described herein, for use in preparing a pharmaceutical formulation for administration, in particular oral administration, to a mammal, in particular a human, suffering from an androgen receptor (AR)-related disease or condition, in particular cancer, more in particular prostate cancer, including but not limited to castration-resistant prostate cancer, metastatic castration resistant prostate cancer, chemotherapy-naive metastatic castration resistant prostate cancer, biochemically relapsed hormone sensitive prostate cancer, or high-risk, non-metastatic castration-resistant prostate cancer.

The present invention also concerns the use of a solid dispersion or particles as described herein, for the preparation of a pharmaceutical formulation for administration, in particular oral administration, to a mammal, in particular a human, suffering from an androgen receptor (AR)-related disease or condition, in particular cancer, more in particular prostate cancer, including but not limited to castration-resistant prostate cancer, metastatic castration resistant prostate cancer, chemotherapy-naive metastatic castration resistant prostate cancer, biochemically relapsed hormone sensitive prostate cancer, or high-risk, non-metastatic castration-resistant prostate cancer.

The invention also relates to a method of treating an androgen receptor (AR)-related disease or condition, in particular cancer, more in particular prostate cancer, including but not limited to castration-resistant prostate cancer, metastatic castration resistant prostate cancer, chemotherapy-naive metastatic castration resistant prostate cancer, biochemically relapsed hormone sensitive prostate cancer, or high-risk, non-metastatic castration-resistant prostate cancer, in a mammal, in particular a human, which comprises administering, in particular orally, to said mammal, in particular human, an effective anticancer amount of a pharmaceutical formulation as described herein.

The invention further concerns the use of a pharmaceutical formulation as specified herein, for the manufacture of a medicament for treating an androgen receptor (AR)-related disease or condition, in particular cancer, more in particular prostate cancer, including but not limited to castration-resistant prostate cancer, metastatic castration resistant prostate cancer, chemotherapy-naive metastatic castration resistant prostate cancer, biochemically relapsed hormone sensitive prostate cancer, or high-risk, non-metastatic castration-resistant prostate cancer. Or, alternatively, the invention concerns a pharmaceutical formulation as specified herein for use in the treatment of an androgen receptor (AR)-related disease or condition, in particular cancer, more in particular prostate cancer, including but not limited to castration-resistant prostate cancer, metastatic castration resistant prostate cancer, chemotherapy-naive metastatic castration resistant prostate cancer, biochemically relapsed hormone sensitive prostate cancer, or high-risk, non-metastatic castration-resistant prostate cancer.

The invention also relates to a pharmaceutical package suitable for commercial sale comprising a container, a pharmaceutical formulation as described herein, and associated with said package written matter.

The term "about" as used herein in connection with a numerical value is meant to have its usual meaning in the context of the numerical value. Where necessary the word "about" may be replaced by the numerical value ±10%, or ±5%, or ±2%, or ±1%. All documents cited herein are incorporated by reference in their entirety.

The following examples are intended to illustrate the present invention.

Example 1: ARN-509 Forms

For the preparation of different (crystalline) forms of ARN-509, reference is made to WO2013/184681, which is incorporated herein by reference. Different (crystalline or amorphous) forms of ARN-509 can be used to prepare the solid dispersions, particles or formulations according to the present invention.

A preferred form of ARN-509 for use in the preparation of a solid dispersion, particle or formulation according to the present invention is ARN-509 Form B, which is an anhydrous crystal. It was prepared by suspending ARN-509 Form A (reference is made to WO2013/184681, including for the diffraction data) in USP water and heating the slurry to 55±5° C., holding at said temperature for at least 24 hours, followed by cooling the slurry to 25±5° C. The resulting slurry was filtered, and the wet cake washed once with USP water. The wet cake was unloaded from the filter and dried under vacuum to afford ARN-509 Form B. Reference is also made to Example 2 below.

Solubility of Form A: 0.01 mg/ml in water.
Solubility of Form B: 0.004 mg/ml in water.

Example 2

Characterisation of ARN-509 Form B
Powder XRD
X-ray powder diffraction (XRPD) analyses were carried out on a PANalytical (Philips) X'PertPRO MPD diffractometer. The instrument is equipped with a Cu LFF X-ray tube.

The compound was spread on a zero background sample holder.

Instrument Parameters
generator voltage: 45 kV
generator amperage: 40 mA
geometry: Bragg-Brentano
stage: spinner stage
Measurement Conditions
scan mode: continuous
scan range: 3 to 50° 2θ
step size: 0.02°/step
counting time: 30 sec/step
spinner revolution time: 1 sec
radiation type: CuKα

| Incident beam path | | Diffracted beam path | |
|---|---|---|---|
| program. divergence slit: | 15 mm | long anti scatter shield: | + |
| Soller slit: | 0.04 rad | Soller slit: | 0.04 rad |
| beam mask: | 15 mm | Ni filter: | + |
| anti scatter slit: | 1° | detector: | X'Celerator |
| beam knife: | + | | |

Figure 1:
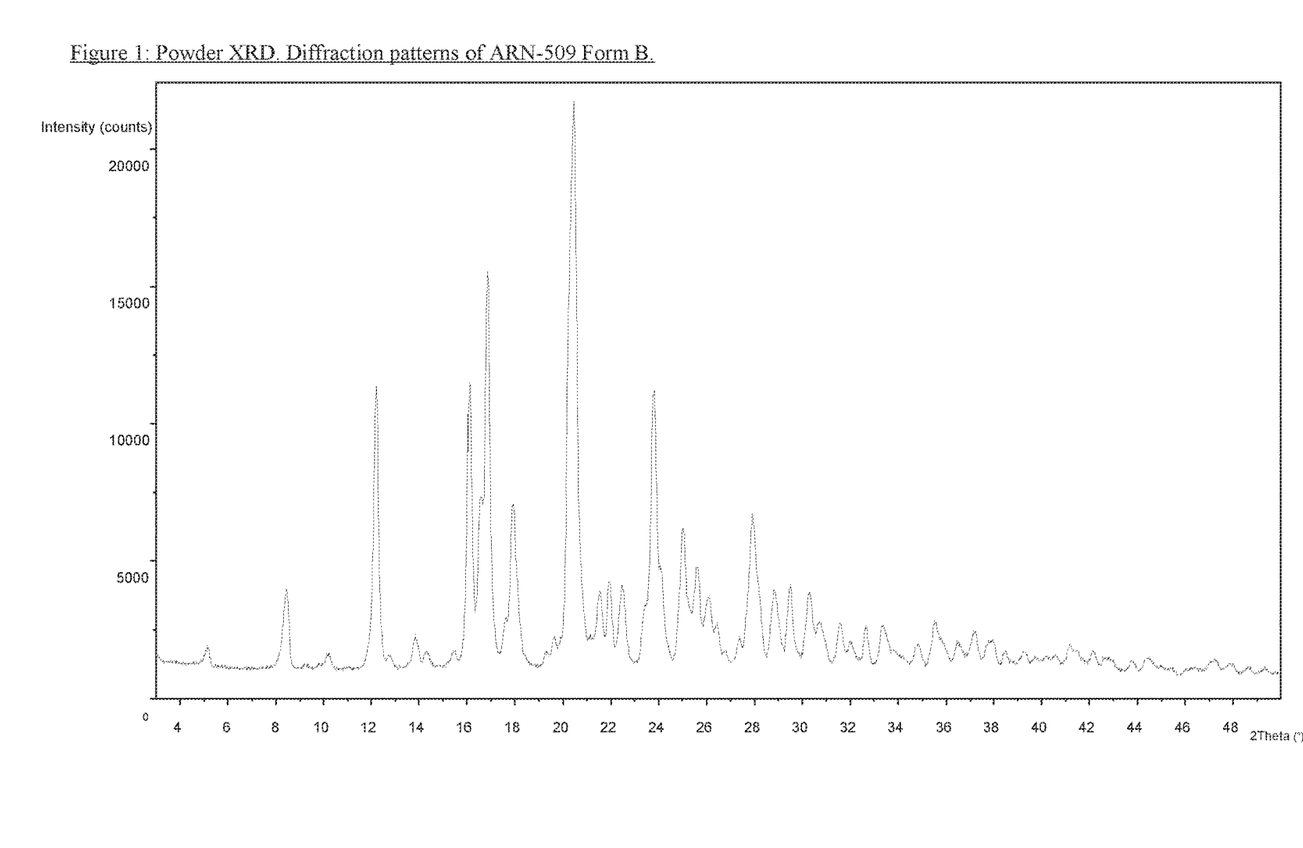
FIG. 1: XRD pattern of ARN-509 Form B.

The X-ray powder diffraction pattern of ARN-509 Form B shows diffraction peaks without the presence of a halo, indicating that this compound is present as a crystalline product. The XRD pattern of ARN-509 Form B is shown in FIG. 1.

Infrared Spectrometry (Micro ATR-IR)

Figure 2:
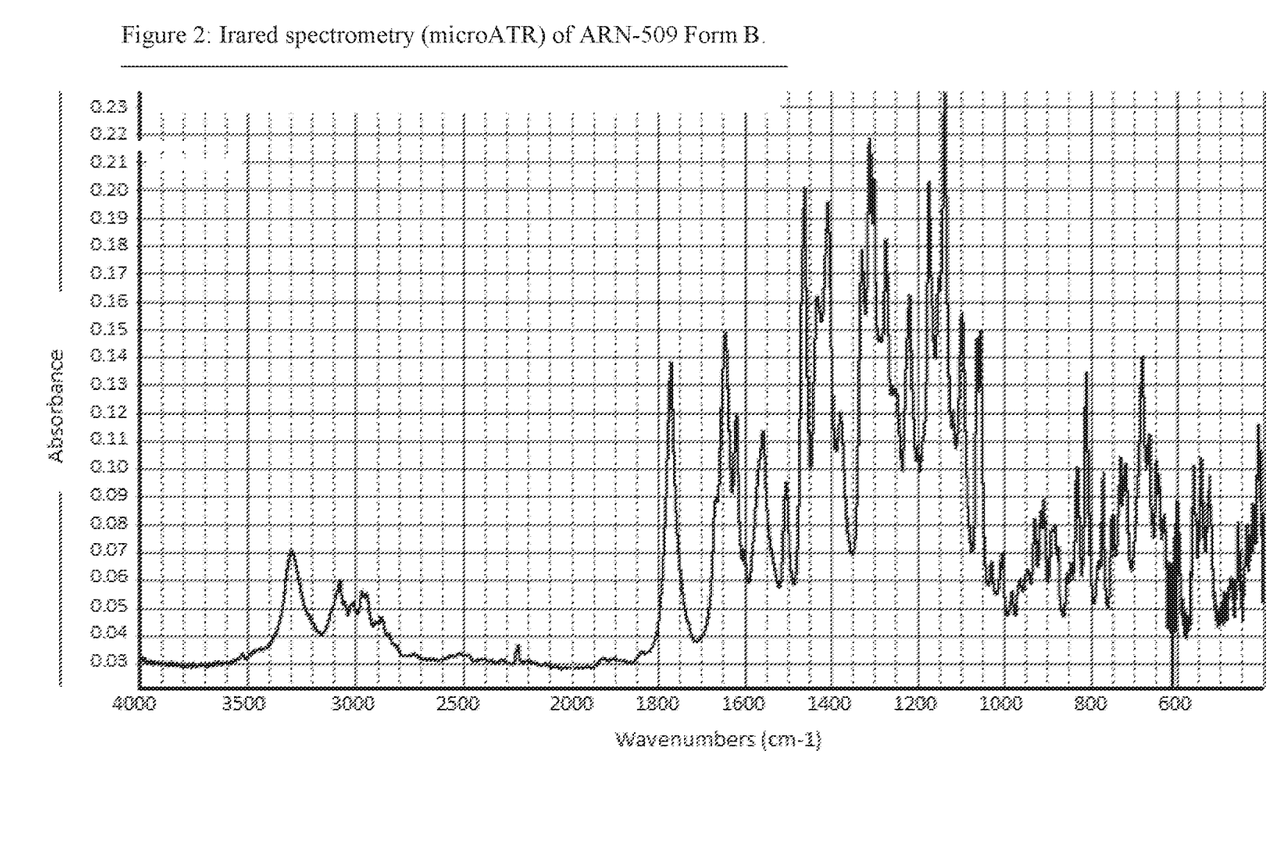
FIG. 2: IR spectrum of ARN-509 Form B.

The samples were analyzed using a suitable microATR accessory.

apparatus: Thermo Nexus 670 FTIR spectrometer
number of scans: 32
resolution: 1 cm$^{-1}$
wavelength range: 4000 to 400 cm$^{-1}$
detector: DTGS with KBr windows
beamsplitter: Ge on KBr
micro ATR accessory: Harrick Split Pea with Si crystal The spectrum of ARN-509 Form B is shown in FIG. 2.

Differential Scanning Calorimetry (DSC)

The compound was transferred into a standard aluminum TA-Instrument sample pan. The sample pan was closed with the appropriate cover and the DSC curve was recorded on a TA-Instruments Q1000 MTDSC equipped with a RCS cooling unit, using the following parameters:

initial temperature: 25° C.
heating rate: 10° C./min
final temperature: 250° C.

Figure 3:
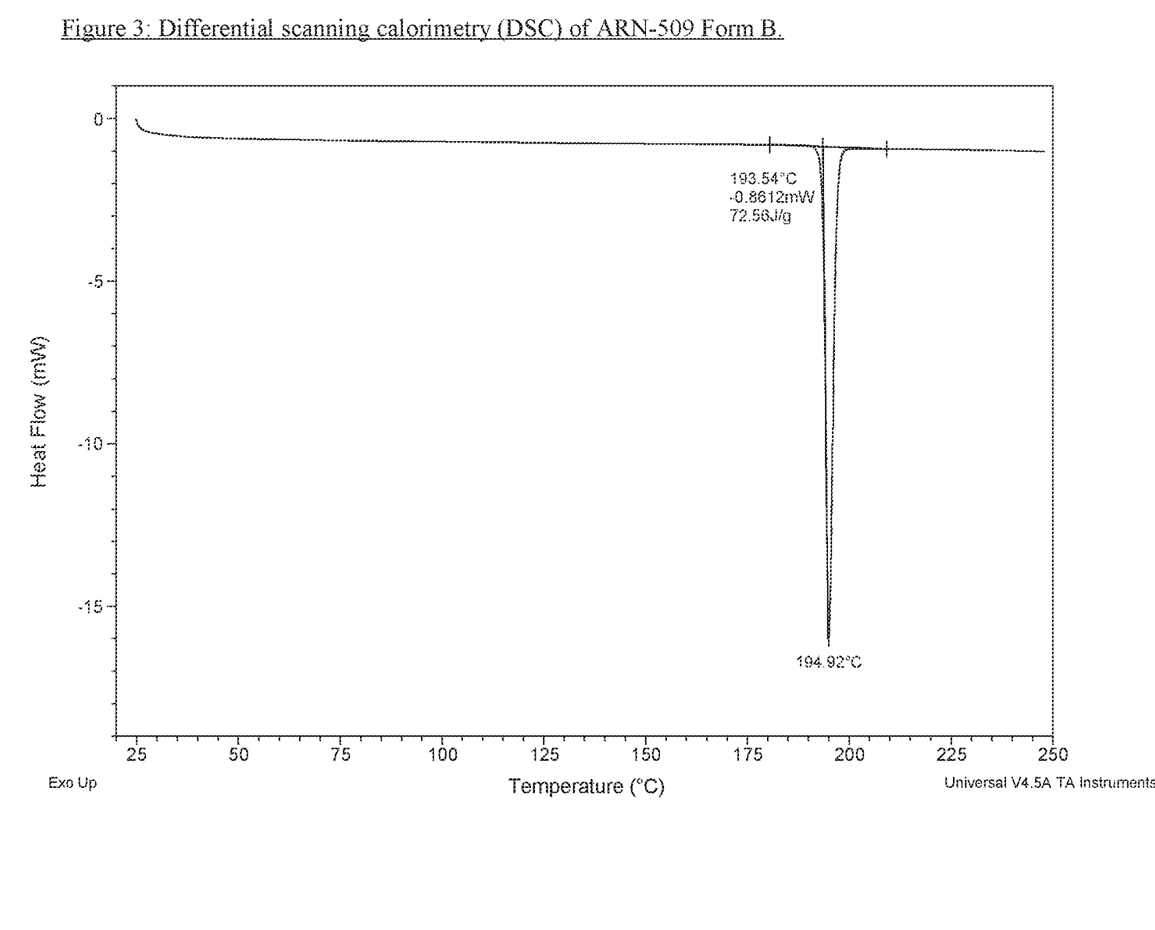
FIG. 3: DSC curve of ARN-509 Form B.

The DSC curve of ARN-509 Form B shows the melting of the product at 194.9° C. with a heat of fusion of 73 J/g. See FIG. 3.

Example 3.1: Preparation of a Solid Dispersion of ARN-509:Eudragit® L-100-55:HPMCAS LG 1:1.5:1.5

| ARN-509 | 250.0 mg |
| Eudragit ® L-100-55 | 375.0 mg |
| HPMCAS LG | 375.0 mg |
| Dichloromethane, $^a$ | 9500.0 mg |
| Methanol $^a$ | 9500.0 mg |

$^a$ Removed during processing
(the reported amounts are for 1 g of SDP (spray dried product))

The dichloromethane and methanol were transferred into a suitable container and stirring was started. Under continuous stirring ARN509 Form B was added to the solvent mixture and stirred until dissolved. Eudragit® L 100-55 was added to the mixture and stirred. The HPMCAS LG was added to the mixture and the complete mixture was stirred overnight. When the ingredients were completely mixed, the mixture was spray dried using a suitable spray dryer, e.g. Buchi mini spray dryer with the following parameters: spray rate in the range from 7.3-7.5 gram/minutes, outlet temperature in the range from 40° C.-42° C. and condenser temperature in the range from −19° C. to −20° C. The spray dried product (SDP) was dried in a suitable dryer, e.g. tray dryer using vacuum, nitrogen flow and a drying temperature of 40° C.

In an analoguous way as described in Example 3.1, the following spray dried products were prepared:

SDP of ARN-509:EUDRAGIT® L 100-55:HPMCAS LG: 1:0.75:2.25 (spray dried from a mixture in dichloromethane/methanol 40/60)

SDP of ARN-509:EUDRAGIT® L 100-55:HPMCAS LG: 1:2.25:0.75 (spray dried from a mixture in dichloromethane/methanol 50/50)

Example 3.2: Preparation of Tablets Comprising a Solid Dispersion of ARN-509:EUDRAGIT® L 100-55:HPMCAS LG: 1:1.5:1.5

| Spray dried powder of 3.1 (SDP) | 240.0 mg |
| Colloidal Anhydrous Silica | 9.1 mg |
| Croscarmellose sodium | 35.0 mg |
| Silicified Microcrystalline Cellulose | 412.4 mg |
| Magnesium stearate | 3.5 mg |

(amounts for 1 tablet)

The SDP, part (2955/4124) of the silicified microcrystalline cellulose, part (10/13) of the colloidal anhydrous silica and part (1/2) of the croscarmellose sodium were sieved (950 μm) and mixed to a homogenous blend using a suitable blender. A dry granulate was made by using a suitable compaction technique. The remainder of the silicified microcrystalline cellulose (1169/4124), colloidal anhydrous silica (3/13) and croscarmellose sodium (1/2) were sieved and added to the dry granulate and further mixed using a suitable blender. Magnesium stearate was sieved and added to the blend and mixed further using a suitable blender. The blend was compressed into tablets using an eccentric tabletting press.

In an analoguous way as described in Example 3.2, the following tablets 3.3 and 3.4 were prepared:

| Tablet 3.3 | |
|---|---|
| SDP of ARN-509:EUDRAGIT ® L 100-55:HPMCAS LG: 1:0.75:2.25 | 240.0 mg |
| Colloidal Anhydrous Silica | 9.1 mg |
| Croscarmellose sodium | 35.0 mg |
| Silicified Microcrystalline Cellulose | 412.4 mg |
| Magnesium stearate | 3.5 mg |

(amounts for 1 tablet)

| Tablet 3.4 | |
|---|---|
| SDP of ARN-509:EUDRAGIT ® L 100-55:HPMCAS LG: 1:2.25:0.75 | 240.0 mg |
| Colloidal Anhydrous Silica | 9.1 mg |
| Croscarmellose sodium | 35.0 mg |
| Silicified Microcrystalline Cellulose | 412.4 mg |
| Magnesium stearate | 3.5 mg |

(amounts for 1 tablet)

Example 4.1: Preparation of a Solid Dispersion of ARN-509:EUDRAGIT® L 100-55:HPMCAS LG: 1:1.5:1.5 by Hot Melt Extrusion (HME)

| ARN-509 | 250.0 mg |
| Eudragit ® L-100-55 | 375.0 mg |
| HPMCAS LG | 375.0 mg |

(the reported amounts are for 1 g of HME product)

The HPMCAS LG, EUDRAGIT® L 100-55, and ARN-509 Form B, were blended in a suitable recipient using a suitable blender. Hot melt extrusion was performed in a suitable extruder, maximum temperature 165° C., screw speed 80 rpm. The hot melt extrudate was collected and milled in a suitable mill. The milled hot melt extrudate was sieved using a suitable sieve.

Example 4.2: Preparation of Tablets Comprising a Solid Dispersion of ARN-509:EUDRAGIT® L 100-55:HPMCAS LG: 1:1.5:1.5

| | |
|---|---|
| HME powder of 4.1 | 240.0 mg |
| Colloidal Anhydrous Silica | 9.1 mg |
| Croscarmellose sodium | 35.0 mg |
| Silicified Microcrystalline Cellulose | 412.4 mg |
| Magnesium stearate | 3.5 mg |

(amounts for 1 tablet)

The silicified microcrystalline cellulose, croscarmellose sodium, colloidal anhydrous silica and hot melt extrudate were sieved (950 µm) and mixed to a homogenous blend using a suitable blender. Magnesium stearate was sieved and added to the blend and mixed further using a suitable blender. The blend was compressed into tablets using an eccentric tableting press.

Example 5.1: Preparation of a Solid Dispersion of ARN-509:EUDRAGIT® L 100-55:HPMCAS LG: 1:0.75:2.25 by Hot Melt Extrusion (HME)

| | |
|---|---|
| ARN-509 | 250.0 mg |
| Eudragit® L-100-55 | 187.5 mg |
| HPMCAS LG | 562.5 mg |

(the reported amounts are for 1 g of HME product)

The HPMCAS LG, EUDRAGIT® L 100-55, and ARN-509 Form B, were blended in a suitable recipient using a suitable blender. Hot melt extrusion was performed in a suitable extruder, maximum temperature 170° C., screw speed 80 rpm. The hot melt extrudate was collected and milled in a suitable mill. The milled hot melt extrudate was sieved using a suitable sieve.

Example 5.2: Preparation of Tablets Comprising a Solid Dispersion of ARN-509:EUDRAGIT® L 100-55:HPMCAS LG: 1:0.75:2.25

| | |
|---|---|
| HME powder of 5.1 | 240.0 mg |
| Colloidal Anhydrous Silica | 9.1 mg |
| Croscarmellose sodium | 35.0 mg |
| Silicified Microcrystalline Cellulose | 412.4 mg |
| Magnesium stearate | 3.5 mg |

(amounts for 1 tablet)

The silicified microcrystalline cellulose, croscarmellose sodium, colloidal anhydrous silica and hot melt extrudate were sieved (950 µm) and mixed to a homogenous blend using a suitable blender. Magnesium stearate was sieved and added to the blend and mixed further using a suitable blender. The blend was compressed into tablets using an eccentric tableting press.

Example 6.1: Preparation of a Solid Dispersion of ARN-509:EUDRAGIT® L 100-55:HPMCAS LG: 1:2.25:0.75 by Hot Melt Extrusion (HME)

| | |
|---|---|
| ARN-509 | 250.0 mg |
| Eudragit® L-100-55 | 562.5 mg |
| HPMCAS LG | 187.5 mg |

(the reported amounts are for 1 g of HME product)

The HPMCAS LG, EUDRAGIT® L 100-55, and ARN-509 Form B, were blended in a suitable recipient using a suitable blender. Hot melt extrusion was performed in a suitable extruder, maximum temperature 165° C., screw speed 80 rpm. The hot melt extrudate was collected and milled in a suitable mill. The milled hot melt extrudate was sieved using a suitable sieve.

Example 6.2: Preparation of Tablets Comprising a Solid Dispersion of ARN-509:EUDRAGIT® L 100-55:HPMCAS LG: 1:2.25:0.75

| | |
|---|---|
| HME powder of 6.1 | 240.0 mg |
| Colloidal Anhydrous Silica | 9.1 mg |
| Croscarmellose sodium | 35.0 mg |
| Silicified Microcrystalline Cellulose | 412.4 mg |
| Magnesium stearate | 3.5 mg |

(amounts for 1 tablet)

The silicified microcrystalline cellulose, croscarmellose sodium, colloidal anhydrous silica and hot melt extrudate were sieved (950 µm) and mixed to a homogenous blend using a suitable blender. Magnesium stearate was sieved and added to the blend and mixed further using a suitable blender. The blend was compressed into tablets using an eccentric tableting press.

Example 7: In Vitro Dissolution Study

Dissolution Method

The tablets were brought in 300 ml of SGFsp (Simulated Gastric Fluid sine pepsin) for 15 minutes, paddle, 100 rpm (rounds per minute), afterwards in 900 ml of FaSSIF (Fasted State Simulated Intestinal fluid), paddle, 100 rpm. % dissolved ARN-509 was measured with UHPLC-UV detection at 242 nm.

The dose per vessel was 120 mg. 60 mg tablets were used. Two tablets per vessel.

Results (% Dissolved as a Function of Time (Minutes).

| | Time (minutes) | | | | | | | | | | |
|---|---|---|---|---|---|---|---|---|---|---|---|
| | 5 | 14 | 20 | 25 | 35 | 45 | 60 | 75 | 105 | 135 | 285 |
| Tablets of Ex 3.2 | 4.3 | 6.9 | 67.3 | 73.5 | 73.6 | 73.0 | 71.4 | 71.7 | 68.4 | 66.5 | 63.7 |
| | 4.4 | 6.9 | 65.6 | 69.8 | 70.5 | 69.4 | 68.4 | 66.9 | 65.0 | 63.4 | 56.9 |
| Tablets 3.3 | 4.3 | 6.2 | 54.1 | 64.4 | 66.6 | 66.9 | 66.4 | 66.9 | 62.4 | 64.0 | 61.7 |
| | 4.1 | 6.4 | 54.9 | 62.0 | 59.8 | 64.5 | 59.7 | 63.3 | 63.2 | 61.9 | 58.8 |
| Tablets | 4.6 | 7.1 | 77.1 | 77.5 | 75.9 | 72.5 | 69.1 | 64.2 | 65.2 | 61.0 | 57.1 |

-continued

| | Time (minutes) | | | | | | | | | | |
|---|---|---|---|---|---|---|---|---|---|---|---|
| | 5 | 14 | 20 | 25 | 35 | 45 | 60 | 75 | 105 | 135 | 285 |
| 3.4 | 4.6 | 7.2 | 75.5 | 77.4 | 75.3 | 72.7 | 66.7 | 66.4 | 64.2 | 59.9 | 44.2 |
| Tablets of Ex 4.2 | 3.1 | 4.7 | 78.4 | 88.7 | 86.8 | 85.7 | 84.5 | 73.7 | 37.6 | 24.3 | 19.5 |
| | 3.2 | 4.8 | 78.3 | 88.0 | 83.8 | 85.9 | 84.2 | 62.2 | 29.0 | 22.7 | 18.9 |
| Tablets of Ex 5.2 | 3.5 | 5.3 | 61.7 | 77.9 | 80.3 | 80.4 | 79.0 | 76.4 | 75.5 | 75.0 | 59.2 |
| | 3.3 | 5.4 | 66.7 | 79.0 | 81.3 | 79.8 | 77.5 | 78.0 | 74.3 | 71.8 | 57.4 |
| Tablets of Ex 6.2 | 2.2 | 3.4 | 76.7 | 85.2 | 85.1 | 78.5 | 49.8 | 21.4 | 17.7 | 17.1 | 15.7 |

The invention claimed is:

1. A solid dispersion comprising ARN-509, a poly(meth)acrylate copolymer and hydroxypropyl methylcellulose acetate succinate.

2. A solid dispersion according to claim 1 wherein the dispersion consists of ARN-509, a poly(meth)acrylate copolymer and hydroxypropyl methylcellulose acetate succinate.

3. A solid dispersion according to claim 1 wherein the weight-by-weight ratio of ARN-509:(poly(meth)acrylate copolymer and hydroxypropyl methylcellulose acetate succinate in the solid dispersion is in the range from 1:1 to 1:5.

4. A solid dispersion according to claim 3 wherein the weight-by-weight ratio of ARN-509:(poly(meth)acrylate copolymer hydroxypropyl methylcellulose acetate succinate in the solid dispersion is 1:3.

5. A solid dispersion according to claim 1 wherein the weight-by-weight ratio of poly(meth)acrylate copolymer to hydroxypropyl methylcellulose acetate succinate in the solid dispersion ranges from 5:95 to 95:5.

6. A The solid dispersion according to claim 5 wherein the weight-by-weight ratio of poly(meth)acrylate copolymer to hydroxypropyl methylcellulose acetate succinate in the solid dispersion ranges from 25:75 to 75:25.

7. A solid dispersion according to claim 6 wherein the weight-by-weight ratio of poly(meth)acrylate copolymer to hydroxypropyl methylcellulose acetate succinate in the solid dispersion is 50:50.

8. A solid dispersion according to claim 1 wherein ARN-509 is present in amorphous form.

9. The solid dispersion according to claim 1 wherein the dispersion is a solid solution.

10. A solid dispersion according to claim 1 wherein the poly(meth)acrylate copolymer is poly(methacrylic acid-co-ethyl acrylate) 1:1.

11. A solid dispersion according to claim 1 wherein the hydroxypropyl methylcellulose acetate succinate is hydroxypropyl methylcellulose acetate succinate granular grade.

12. A The solid dispersion according to claim 1 obtainable by spray drying.

13. A solid dispersion according to claim 1 obtainable by hot melt extrusion.

14. A particle consisting of a solid dispersion as defined in claim 1.

15. A particle comprising a solid dispersion as defined in claim 2.

16. A pharmaceutical formulation comprising a pharmaceutically acceptable carrier and a solid dispersion according to claim 1.

17. A pharmaceutical formulation comprising a pharmaceutically acceptable carrier and a particle according to claim 14.

18. A pharmaceutical formulation according to claim 16 wherein the formulation is a tablet.

19. A formulation according to claim 18 which is suitable for oral administration.

20. A process for preparing the solid dispersion according to claim 12 comprising the steps of mixing ARN-509, a poly(meth)acrylate copolymer and hydroxypropyl methylcellulose acetate succinate in a suitable solvent and spray drying said mixture.

21. The process according to claim 20 wherein the suitable solvent is a mixture of dichloromethane and methanol.

22. The process according to claim 21 wherein the weight:weight ratio of dichloromethane to methanol in the mixture is 50:50.

23. A solid dispersion according to claim 3 wherein the weight-by-weight ratio of ARN-509:(poly(meth)acrylate copolymer and hydroxypropyl methylcellulose acetate succinate) in the solid dispersion is 1:2.

24. The formulation according to claim 17 wherein the formulation comprises 60 mg of ARN-509.

25. A pharmaceutical formulation according to claim 17 wherein the formulation comprises 120 mg of ARN-509.

26. A pharmaceutical formulation according to claim 17 wherein the formulation comprises 240 mg of ARN-509.

27. A pharmaceutical formulation comprising a pharmaceutically acceptable carrier and a particle according to claim 15.

28. A pharmaceutical formulation according to claim 27 wherein the formulation is a tablet.

29. A pharmaceutical formulation according to claim 28 which is suitable for oral administration.

30. A pharmaceutical formulation according to claim 18 wherein the formulation comprises 60 mg of ARN-509.

31. A pharmaceutical formulation according to claim 18 wherein the formulation comprises 120 mg of ARN-509.

32. A pharmaceutical formulation according to claim 18 wherein the formulation comprises 240 mg of ARN-509.

33. A pharmaceutical formulation according to claim 17 wherein the weight of the solid dispersion is from 20 to 40% of the total weight of the formulation.

34. A pharmaceutical formulation according to claim 24 wherein the weight of the solid dispersion is from 20 to 40% of the total weight of the formulation.

35. A pharmaceutical formulation according to claim 25 wherein the weight of the solid dispersion is from 20 to 40% of the total weight of the formulation.

36. A pharmaceutical formulation according to claim 26 wherein the weight of the solid dispersion is from 20 to 40% of the total weight of the formulation.

37. A pharmaceutical formulation according to claim 18 wherein the weight of the solid dispersion is from 20 to 40% of the total weight of the formulation.

38. A pharmaceutical formulation according to claim 30 wherein the weight of the solid dispersion is from 20 to 40% of the total weight of the formulation.

39. A pharmaceutical formulation according to claim 31 wherein the weight of the solid dispersion is from 20 to 40% of the total weight of the formulation.

40. A pharmaceutical formulation according to claim 32 wherein the weight of the solid dispersion is from 20 to 40% of the total weight of the formulation.

41. A pharmaceutical formulation according to claim 17 further comprising a second anticancer agent.

42. A pharmaceutical formulation according to claim 41 wherein the second anticancer agent is an androgen biosynthesis inhibitor.

43. The pharmaceutical formulation according to claim 42 wherein the second anticancer agent is abiraterone acetate.

* * * * *